US010535446B2

(12) United States Patent
Seifert et al.

(10) Patent No.: US 10,535,446 B2
(45) Date of Patent: Jan. 14, 2020

(54) MEDICAL ELECTRICAL LEAD JOINTS AND METHODS OF MANUFACTURE

(71) Applicant: Medtronic, Inc., Minneapolis, MN (US)

(72) Inventors: Kevin R. Seifert, Forest Lake, MN (US); Kathleen M. Grenz, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 660 days.

(21) Appl. No.: 15/231,485

(22) Filed: Aug. 8, 2016

(65) Prior Publication Data

US 2016/0351293 A1 Dec. 1, 2016

Related U.S. Application Data

(63) Continuation of application No. 12/627,052, filed on Nov. 30, 2009, now abandoned.
(Continued)

(51) Int. Cl.
*A61N 1/05* (2006.01)
*B29C 65/00* (2006.01)
(Continued)

(52) U.S. Cl.
CPC .............. *H01B 7/0216* (2013.01); *A61B 5/05* (2013.01); *A61N 1/04* (2013.01); *A61N 1/36* (2013.01);
(Continued)

(58) Field of Classification Search
CPC . A61N 1/04; A61N 1/05; A61N 1/056; A61N 1/0563; B29C 65/00; B29C 65/02; B29C 65/08; B29C 65/10; B29C 65/14; B29C 65/16; B29C 65/18; B29C 65/48; B29C 65/483; B29C 65/52; B29C 65/524; B29C 65/525; B29C 65/72; B29C 66/00; B29C 66/301; B29C 66/50; B29C 66/5221; B29C 66/61; B29C 66/612; B29C 66/712; B29C 48/09; B29C 48/21; H01R 2201/12; H01R 4/70; B32B 2597/00; B32B 1/08
USPC ........ 156/47, 48, 49, 51, 52, 53, 54, 55, 56, 156/60, 70, 143, 144, 184, 185, 187, 188, 156/190, 191, 192, 195, 242, 243, 244.11, 156/244.12, 244.13, 272.2, 273.9, 274.2, 156/293, 294, 296, 306.6, 308.2, 309.6;
(Continued)

(56) References Cited

U.S. PATENT DOCUMENTS 4,481,953 A 11/1984 Gold et al.
4,549,684 A * 10/1985 Telly ...................... B23K 20/10
228/110.1
(Continued)

*Primary Examiner* — Philip C Tucker
*Assistant Examiner* — Brian R Slawski

(57) ABSTRACT

A joint between an insulative sidewall of a medical electrical lead subassembly and an underlying fluoropolymer layer includes an interfacial layer. A first section of the interfacial layer is bonded to the fluoropolymer layer and is formed by a thermoplastic fluoropolymer; a second section of the interfacial layer extends adjacent the first section and is bonded to the insulative sidewall. The insulative sidewall, of the subassembly, and the second section, of the interfacial layer, are each formed from a material that is not a fluoropolymer. A recess is formed in the first section of the interfacial layer and the second section of the interfacial layer extends within the recess.

14 Claims, 2 Drawing Sheets

Related U.S. Application Data

(60) Provisional application No. 61/118,601, filed on Nov. 29, 2008.

(51) Int. Cl.

| | | |
|---|---|---|
| *B29C 65/02* | (2006.01) | |
| *B29C 65/48* | (2006.01) | |
| *B29C 65/52* | (2006.01) | |
| *B29C 65/72* | (2006.01) | |
| *B29C 48/21* | (2019.01) | |
| *B32B 37/00* | (2006.01) | |
| *B32B 1/08* | (2006.01) | |
| *H01B 7/02* | (2006.01) | |
| *A61B 5/05* | (2006.01) | |
| *A61N 1/04* | (2006.01) | |
| *A61N 1/36* | (2006.01) | |
| *A61N 1/39* | (2006.01) | |
| *B29L 23/00* | (2006.01) | |
| *B29K 627/12* | (2006.01) | |
| *B29K 627/18* | (2006.01) | |
| *B29L 31/34* | (2006.01) | |
| *B29L 31/00* | (2006.01) | |

(52) U.S. Cl.
CPC ............... *A61N 1/39* (2013.01); *B29C 65/02* (2013.01); *B29C 65/48* (2013.01); *B29C 65/524* (2013.01); *B29C 66/028* (2013.01); *B29C 66/0224* (2013.01); *B29C 66/30325* (2013.01); *B29C 66/526* (2013.01); *B29C 66/5344* (2013.01); *B29C 66/71* (2013.01); *B29C 66/712* (2013.01); *A61B 2562/125* (2013.01); *B29C 66/1122* (2013.01); *B29K 2627/12* (2013.01); *B29K 2627/18* (2013.01); *B29K 2995/0005* (2013.01); *B29L 2023/007* (2013.01); *B29L 2031/3462* (2013.01); *B29L 2031/753* (2013.01); *Y10T 156/10* (2015.01)

(58) Field of Classification Search
USPC ......... 600/373, 374, 375; 607/115, 116, 119, 607/122, 126
See application file for complete search history.

(56) References Cited

U.S. PATENT DOCUMENTS

| | | |
|---|---|---|
| 4,603,705 A | 8/1986 | Speicher et al. |
| 5,105,826 A | 4/1992 | Smits et al. |
| 5,174,288 A | 12/1992 | Bardy et al. |
| 5,271,417 A | 12/1993 | Swanson et al. |
| 5,522,872 A | 6/1996 | Hoff |
| 5,676,694 A | 10/1997 | Boser et al. |
| 5,728,149 A | 3/1998 | Laske et al. |
| 5,897,537 A | 4/1999 | Berg et al. |
| 5,928,277 A | 7/1999 | Laske et al. |
| 5,935,159 A | 8/1999 | Cross, Jr. et al. |
| 5,957,970 A | 9/1999 | Shoberg et al. |
| 6,016,436 A | 1/2000 | Bischoff et al. |
| 6,038,463 A | 3/2000 | Laske et al. |
| 6,038,472 A | 3/2000 | Williams et al. |
| 6,052,625 A | 4/2000 | Marshall |
| 6,061,595 A | 5/2000 | Safarevich |
| 6,152,914 A | 11/2000 | Van De Kerkhof et al. |
| 6,181,971 B1 | 1/2001 | Doan |
| 6,245,053 B1 | 6/2001 | Benjamin |
| 6,256,542 B1 | 7/2001 | Marshall et al. |
| 6,259,954 B1 | 7/2001 | Conger et al. |
| 6,289,251 B1 | 9/2001 | Huepenbecker et al. |
| 6,500,285 B2 | 12/2002 | Pepin et al. |
| 6,615,695 B1 | 9/2003 | Hjelle et al. |
| 6,697,675 B1 | 2/2004 | Safarevich et al. |
| 6,704,604 B2 * | 3/2004 | Soukup ............... A61N 1/0563 607/116 |
| 6,801,809 B2 | 10/2004 | Laske et al. |
| 6,813,521 B2 | 11/2004 | Bischoff et al. |
| 6,920,361 B2 | 7/2005 | Williams |
| 7,031,777 B2 | 4/2006 | Hine et al. |
| 7,130,700 B2 | 10/2006 | Gardeski et al. |
| 7,277,762 B2 | 10/2007 | Belden et al. |
| 7,474,924 B2 | 1/2009 | Honeck et al. |
| 7,512,447 B2 | 3/2009 | Marshall et al. |
| 2005/0240252 A1 | 10/2005 | Boser et al. |
| 2007/0276458 A1 | 11/2007 | Boser |
| 2008/0057784 A1* | 3/2008 | Zarembo ............... A61N 1/056 439/592 |
| 2009/0012591 A1* | 1/2009 | Barker ..................... A61N 1/05 607/116 |
| 2009/0254162 A1 | 10/2009 | Quinci et al. |
| 2009/0318999 A1 | 12/2009 | Hall |

* cited by examiner

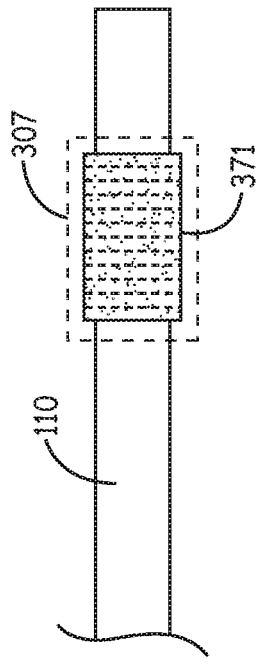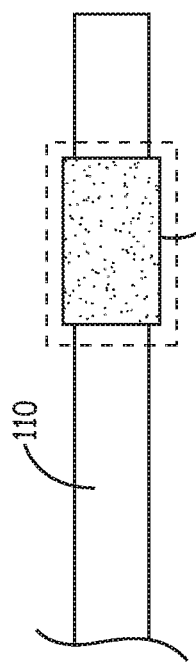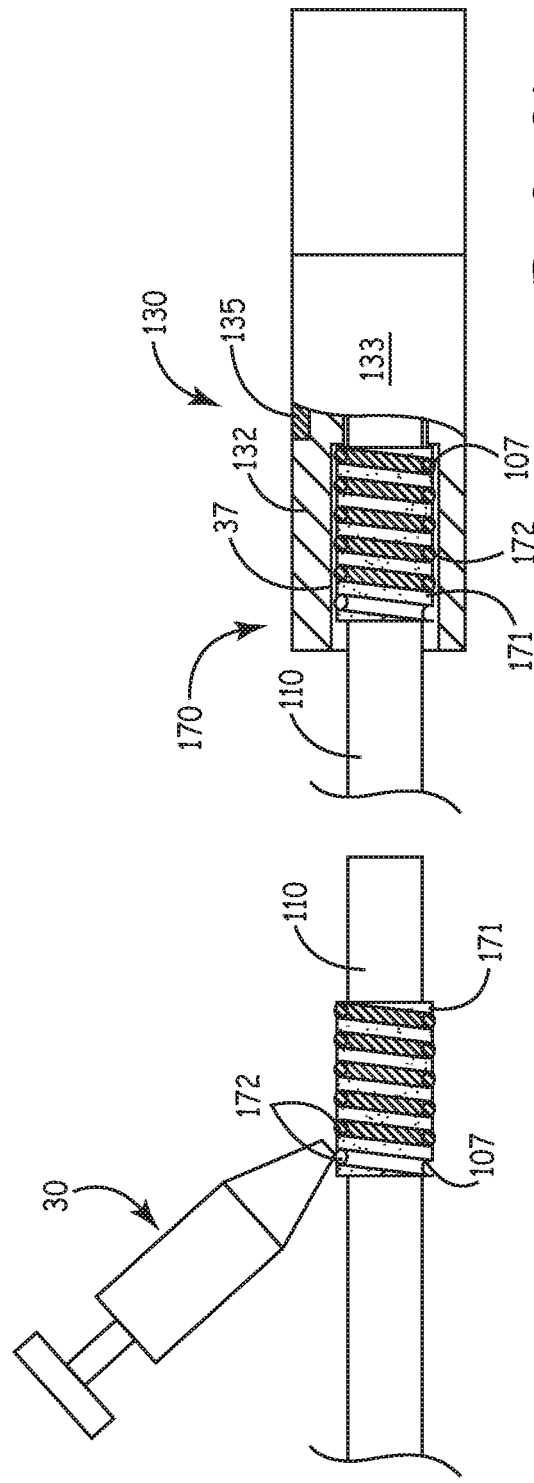

MEDICAL ELECTRICAL LEAD JOINTS AND METHODS OF MANUFACTURE

CROSS-REFERENCE TO RELATED APPLICATIONS

This application is a Continuation Application of U.S. patent application Ser. No. 12/627,052, filed on Nov. 30, 2009, now abandoned, and also claims benefit of U.S. Provisional Application No. 61/118,601, filed on Nov. 29, 2008. The disclosure of the above applications is incorporated herein by reference.

TECHNICAL FIELD

The present disclosure pertains to medical electrical leads and more particularly to joints thereof, which include fluoropolymers.

BACKGROUND

Fluoropolymer materials, such as polytetrafluoroethylene (PTFE) and Ethylene Tetrafluoroethylene (ETFE), have been used in the construction of medical electrical leads, for example, to provide lubricious and insulative layers surrounding one or more conductors of the leads. The lubricity of fluoropolymers can provide benefits for both the manufacturing of the leads and for some functional aspects of the leads, as is well known to those skilled in the art. However, fluoropolymer materials can present some challenges for lead construction, for example, in forming sufficiently strong and relatively low profile joints between these materials and other, non-fluoropolymer, materials, which form other insulative members of the leads, for example, included in connector and/or electrode subassemblies of the leads. In U.S. patent application Ser. No. 11/549,284 filed Oct. 13, 2006 discloses one mechanism for providing such joints.

SUMMARY OF THE INVENTION

The invention relates to medical electrical leads of the type comprising an elongate conductor, an inner insulative layer formed from a first material, typically surrounding the conductor, and an insulative sidewall member formed from a second material mounted thereabout. A conductive member such as an electrode or a n electrical connector is typically mounted about the insulative sidewall. In the disclosed embodiments, one of the first and second materials is a fluoropolymer and the other is not. The invention comprises methods and mechanisms for providing a joint between the inner insulative layer and the insulative sidewall of the subassembly.

Like the joint described in the above-cited Boser application, the joint is formed by an interfacial layer extending between an outer surface of the inner insulative layer and an inner surface of the insulative sidewall. In these embodiments, the interfacial layer comprises a first section being formed from a third material and being bonded to the outer surface of the inner insulative layer and a second section extending adjacent the first section and being bonded to the inner surface of the insulative sidewall of the subassembly. One of the third and fourth materials comprises a thermoplastic fluoropolymer, and other does not. The respective fluoropolymer materials are bonded to one another as are the respective non-fluoroppolymer materials.

In the context of the present invention, the first section includes an outer surface, facing the inner surface of the insulative sidewall, and having least one groove formed in the outer surface of the first section. The second section in such embodiments extends within the at least one groove. Bonding according to the invention may comprise any known bonding technique, including adhesive bonding, thermal bonding, and the like.

In the specific embodiments discussed below, the inner insulative layer and the first section of the interfacial layer are formed of fluoropolymers and the insulative sidewall and the second section of the interfacial layer are formed of non-fluoropolymers. However, the arrangement may also be reversed, with the inner insulative layer and the first section of the interfacial layer formed of non-fluoropolymers and the insulative sidewall and the second section of the interfacial layer formed of fluoropolymers.

BRIEF DESCRIPTION OF THE DRAWINGS

The following drawings are illustrative of particular embodiments and, therefore, do not limit the scope of the invention. The drawings are not to scale (unless so stated) and are intended for use in conjunction with the explanations in the following detailed description. Embodiments will hereinafter be described in conjunction with the appended drawings, wherein like numerals denote like elements.

FIGS. 2A-D are schematics outlining a sequence of steps for manufacturing a joint, according to a preferred embodiment of the invention.

DETAILED DESCRIPTION

Figure 1:
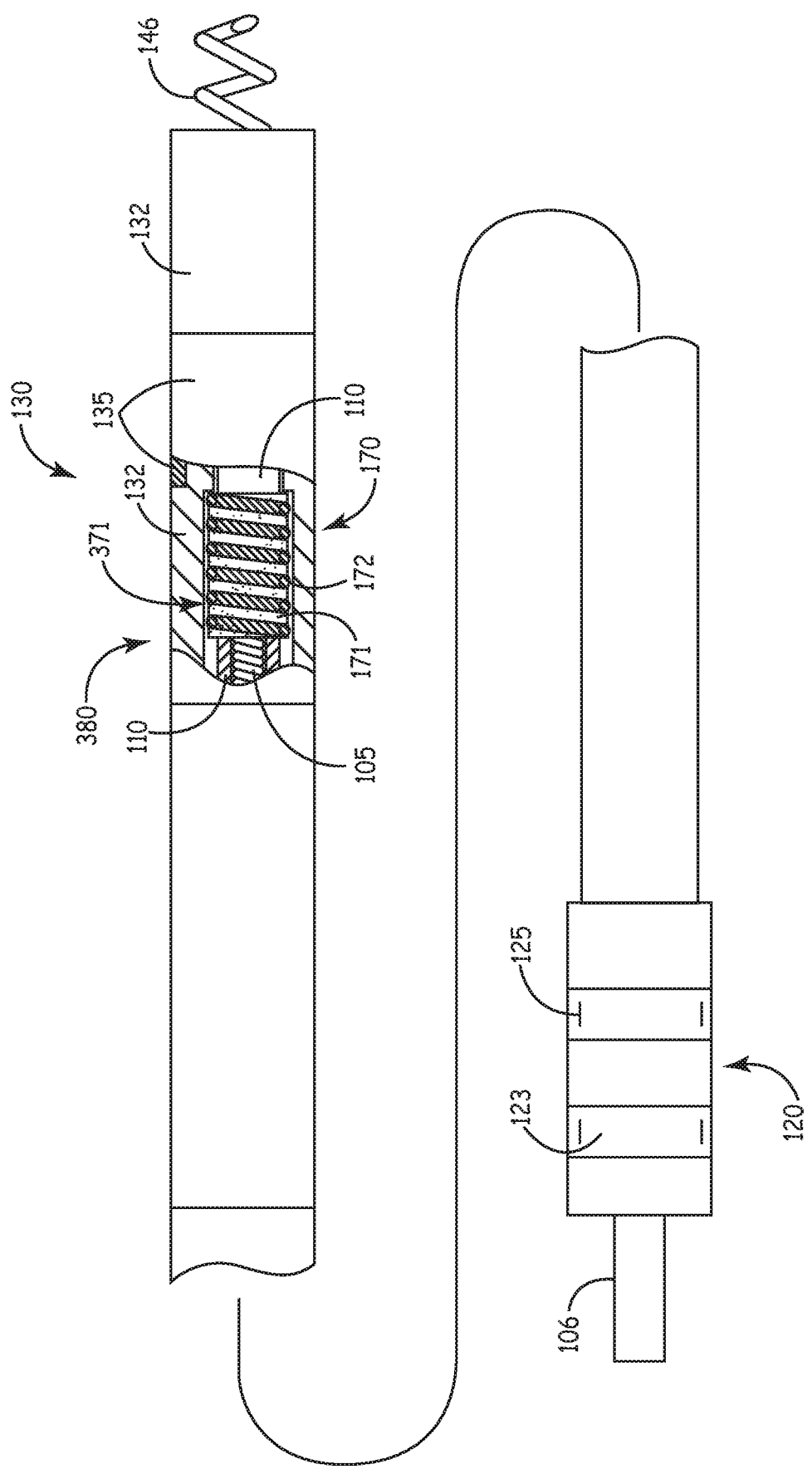
FIG. 1 is a plan view of a medical electrical lead, including cut-away sections showing a joints of the lead, according to the present invention.

The following detailed description is exemplary in nature and is not intended to limit the scope, applicability, or configuration of the invention in any way. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

FIG. 1 is a plan view of a medical electrical lead 100, including cut-away sections showing an exemplary joint 170 according to a preferred embodiment. FIG. 1 illustrates lead 100 including a lead body 109 extending between a proximal connector assembly 120 and a distal electrode assembly 130 including an insulative tubular sidewall 132 carrying ring electrode 135 and housing an helix electrode 146. With further reference to FIG. 1, those skilled in the art will appreciate that a conductor 105 couples helix electrode 146 to a pin contact 106, which is shown extending proximally from connector assembly 120, and that two more conductors (not shown) extend within lead body 109 to couple electrode 135 and electrode 155 to corresponding conductive electrical contacts 123 and 125. Thus, lead 100 is a tripolar lead that may provide pacing and sensing, via electrodes 135 and 146, and defibrillation, via electrode 155; however, it should be noted that embodiments of the present invention are not limited to inclusion in leads like lead 100, and lead 100 is only an exemplary type of lead used for the purpose of illustration.

FIG. 1 further illustrates conductor 105 extending within an inner insulative layer 110, which, according to some embodiments, is formed from single or multiple layers of a fluoropolymer material, for example, PTFE or ETFE, which are both available in tubing form, for medical device applications, from Zeus Industrial Products, Inc. (Orangeburg, S.C.); inner insulative layer 110 is joined to electrode assembly 130, via a joint 170. Joint 170 is formed by an interfacial layer that extends over a length between an outer surface of inner insulative layer 110 and an inner surface of the corresponding insulative sidewall of electrode head member 132. Insulative sidewall 132 is formed by a material that does not comprise a fluoropolymer, examples of which include, without limitation, implantable medical grade polyurethanes and silicone rubbers, which are well known to those skilled in the art, combinations of polyurethane and silicone, for example, PurSil® available from The Polymer Technology Group, Inc, and implantable grade polyetheretherketone (PEEK) high-performance thermoplastic, for example, Invibio® PEEK-OPTIMA® for the medical industry. The interfacial layer of each of joint 170 includes at least two sections, one section compatible for bonding to inner insulative layer 110 and the other section for bonding to insulative sidewall 122. According to some preferred embodiments, inner insulative layer 110 is a tubular member, forming a relatively lubricious liner for conductor 105 to be slideable therein, so that conductor 105 can be used to translate torque from pin contact 106 to helix electrode 146, in order to extend and retract helix electrode 146.

Joint 170 is shown between electrode head assembly and inner insulative layer 110. FIG. 1 illustrates the interfacial layer that forms joint 170 including a first section 171, which is bonded to inner insulative layer 110 and at least one groove 107 formed in an outer surface thereof; first section 171 is formed from a thermoplastic fluoropolymer material. FIG. 1 further illustrates the interfacial layer including a second section 172, which extends adjacent first section 171 and within groove 107; second section 172, is formed from a material that may not comprise a fluoropolymer, and is compatible for bonding with the inner surface of insulative sidewall 132. According to the preferred embodiments, in which inner insulative layer 110 is a tubular member, first section 171 extends about a portion of, or an entirety of the circumference of inner insulative layer 110, and groove 107 extends likewise, for example, as a single groove, along a helical path about the circumference and along a length of first section 171, or as a plurality of grooves, extending about the circumference of first section 171, and being spaced apart from one another along the length of first section 171. (Groove 107 may be better seen in FIG. 2C.) The walls of the groove or recess may be canted (non-perpendicular to the axis of the lead body) to improve interlock or tensile holding force. This geometry may also improve the seal between the layers.

Suitable commercially available thermoplastic fluoropolymer materials, from which first section 171 may be formed, include, without limitation, fluorinated ethylene propylene (FEP) and perfluoroalkoxy copolymer (PFA), for example, available from DuPont™ under the trade name Teflon®, polyvinylidene fluoride (PVDF), such as KYNAR® available from Arkema, Inc. (Philadelphia, Pa.), and terpolymer of tetrafluoroethylene, hexafluoropropylene and vinylidene fluoride (THV); each of these materials are available in tubing form from Zeus Industrial Products, Inc. (Orangeburg, S.C.). According to some exemplary embodiments, first section 171, is thermally bonded to inner insulative layer 110, for example, via a heated die, mold or hot air fixturing, but welding methods, such as laser or ultrasonic welding are contemplated for bonding sections 171 to inner insulative layer 110, as is adhesive bonding. Suitable materials from which second section 172 may be formed, depend upon the material forming insulative sidewall 132 to which second section 172 is bonded. According to some preferred embodiments sidewall 132 is formed from a relatively rigid implantable grade polyurethane material, for example, having a 75D durometer, and the corresponding second section 172 is also formed from a polyurethane material. Second section 172 may be bonded to sidewalls 132 via either thermal or adhesive bonding. Bonding methods for both first section 171 and second section 172 of the interfacial layer of junction 170 are described in greater detail below, in conjunction with FIGS. 2A-D.

Turning now to FIGS. 2A-D, a method for forming a joint according to joint 170 shown in FIG. 1 will be described. FIGS. 2A-D are schematics outlining a sequence of steps for manufacturing a joint 380, which is formed by an interfacial layer between insulative sidewall 132 of electrode subassembly 130 and inner insulative layer 110, according to some embodiments and methods. FIG. 2A illustrates an initial assembly of a section 371 onto inner insulative layer 110 for thermal bonding thereto. FIG. 2B illustrates the thermally bonded section 371 within a forming fixture 307, which is shown schematically by the dashed lines. FIG. 2C illustrates first section 171 of the interfacial layer, having been formed from section 371, via forming fixture 307, to include groove 107, and second section 172 of the interfacial layer being deposited into groove 107. FIG. 2D illustrates insulative sidewall 132 of electrode subassembly 130 placed about first and second sections 171, 172 to complete joint 380 between insulative inner sidewall 110 and subassembly 130.

With reference to FIG. 2A, according to some embodiments, section 371 is initially formed as a tube, and inner insulative layer 110, also tubular, is inserted into a lumen of section 371, prior to thermal bonding. A temporary containment member, shown by dashed lines of FIG. 2A, may be employed in the bonding process. With reference to FIG. 2A, according to some embodiments, first section 371 is initially formed as a tube, and inner insulative layer 110, also tubular, is inserted into a lumen of first section 371, prior to thermal bonding, which bonding is performed by inserting the initial assembly into a die cavity which is subsequently heated to a temperature sufficient to melt first section 371, so that first section 371 bonds to inner insulative layer 110. According to some methods, a temporary containment member, shown with dashed lines in FIG. 2A, for example, a band formed from silicone or another suitable material having a melt temperature higher than that of first section 371, is assembled around first section 371 on inner insulative layer 110, for the thermal bonding process, in order to contain the molten material of first section 371, during and/or following thermal bonding. Once the assembly has cooled, the containment member is removed.

According to some exemplary embodiments, inner insulative layer 110 is a PTFE tube, having a wall thickness between approximately 0.003 inch and approximately 0.004 inch, and first section 371 is an FEP tube having a wall thickness between approximately 0.002 inch and approximately 0.004 inch and a length between approximately 0.04 inch and approximately 0.05 inch. A melt temperature for PTFE is approximately 620° F. and a melt temperature for FEP is in the range of approximately 500° F. to approximately 545° F., thus a suitable temperature for thermal bonding, according to these exemplary embodiments, is between approximately 550° F. and approximately 600° F. According to a laboratory method, which was used to prepare evaluation samples, a silicone tube, having an approximately 0.006 inch wall thickness, was employed as the temporary containment member, described above, so that a temperature of a thermal bonding die cavity, was set to approximately 800° F. and held for a time of approximately 16 seconds in order to thermally bond FEP first sections to underlying PTFE tubes.

According to FIGS. 2B-C, following the thermal bonding, section 371 is transformed into first section 171, by forming groove 107 in an outer surface of section 371. With reference to FIG. 2B, section 371, having been bonded to inner insulative layer 110, is inserted into forming fixture 307, for example, a die whose cavity includes an undulating surface to interface with the outer surface of section 371. According to the exemplary embodiments, wherein inner insulative layer 110 is formed from PTFE, having a thickness of between approximately 0.003 inch and approximately 0.004 inch, and section 371 is formed from FEP, having a thickness between approximately 0.002 inch and approximately 0.004 inch, the die of fixture 307 is brought to a temperature of approximately 485° F. for a time of approximately 16 seconds to form groove 107. According to alternate methods, a single heated die, including the undulating surface to form groove 107, may be used to both thermally bond section 371 to inner insulative layer 110 and to form groove 107 in the outer surface of section 371, for example, by employing those time and temperature parameters described above for the aforementioned exemplary materials and wall thicknesses.

With reference to FIG. 2C, it may be appreciated that groove 107 follows a helical path about a circumference of first section 171; however, according to alternate embodiments, first section 171 includes a plurality of individual grooves spaced apart from one another along a length of thereof. According to some exemplary embodiments, a length of first section 171 is between approximately 0.06 inch and approximately 0.08 inch, a depth of groove 107 (or of each groove of the alternate plurality of grooves) is between approximately 0.002 inch and approximately 0.004 inch, and a width of groove 107 is between approximately 0.003 inch and approximately 0.007 inch. Either a plasma or corona surface treatment, known to those skilled in the art, or other surface treatments that improve 'bondability', may be applied to the outer surface of first section 171, prior to the dispensing of the material forming second section 172, which is illustrated in FIG. 2C. Such a treatment may modify the surface of groove 107 to enhance bonding with the material forming second section 172. According to the illustrated embodiment, second section 172 is in adhesive form and applied with a syringe 30, after which first and second sections 171, 172 may be rolled against a relatively flat surface, to make a profile, or outer diameter, of second section 172 flush with that of first section 171 between the turns of groove 107, prior to curing second section 172. As an alternative to dispensing layer 172, the layer can also be overmolded into layer 171. Also, as an option, layer 132 (outer insulation or proximal sleevehead) can be combined and molded or reflowed into layer 172's groove/recess features.

Once second section 172 has cured, joint 170 may be completed, as illustrated in FIG. 2D, by applying adhesive 37 between the inner surface of insulation sidewall 132 and outer surfaces of sections 171, 172. An adhesive primer may be applied to the outer surfaces of sections 171, 172 and/or to the inner surface of sidewall 132, prior to applying adhesive 37. According to some exemplary embodiments, wherein second section 172 and sidewall 132 are both formed from a polyurethane material, adhesive 37, and the optional primer, are also formed from a polyurethane material, which forms a relatively strong bond therebetween, and a weaker bond between first section 171 and sidewall 132. As an alternative to adhesive 37, a thermal bonding method is contemplated for forming a bond between second section 172 of the interfacial layer and insulative sidewall 132, for example, in a manner previously described; a welding method, either laser or ultrasonic, is also contemplated as an alternative. It should be noted, that for some manufacturing methods, one or more intermediate steps may be taken between the step illustrated by FIG. 2C and that by FIG. 2D. For example, conductors (not shown) for coupling electrodes 135 and 155 (FIG. 1) may be assembled around inner insulative layer 110, and at least the conductor for coupling electrode 135 may be routed through assembly 130 to meet with electrode 135, prior to the step illustrated by FIG. 2D.

In the foregoing detailed description, the invention has been described with reference to specific embodiments. However, it may be appreciated that various modifications and changes can be made without departing from the scope of the invention as set forth in the appended claims. For example, the mechanism for providing the joint 170 may also be applied to couple the inner insulative layer 110 to the outer insulative portion sidewall of the connector assembly 120 as illustrated in FIG. 1.

We claim:

1. A method for manufacturing a joint in a medical electrical lead, the joint being between an inner surface of an insulative sidewall of the lead and an outer surface of a tubular fluoropolymer layer, the method comprising:
    thermally bonding a thermoplastic fluoropolymer layer to the outer surface of the fluoropolymer layer, and providing an outer surface of the thermoplastic fluoropolymer layer with a recess formed therein;
    assembling a layer of another material into the recess formed in the outer surface of the thermoplastic fluoropolymer layer;
    thereafter adhesively bonding the other material layer in the recess formed in the outer surface of the thermoplastic fluoropolymer layer to the inner surface of the insulative sidewall;
    wherein the other material layer and the insulative sidewall are each formed from a material that does not comprise a fluoropolymer; and
    wherein the step of adhesively bonding the other material layer to the inner surface of the insulative sidewall comprises placing an adhesive between the inner surface of the insulative sidewall and the layer of the other material.

2. The method of claim 1, wherein the recess formed within the thermoplastic fluoropolymer layer extends circumferentially around the thermoplastic fluoropolymer layer.

3. The method of claim 2 wherein the recess formed within the thermoplastic fluoropolymer layer comprises a groove.

4. The method of claim 1 wherein the recess formed within the thermoplastic fluoropolymer layer comprises a groove.

5. The method of claim 1 wherein the adhesive is formed from a material that does not comprise a fluoropolymer.

6. The method of claim 1 wherein the step of assembling the layer of the other material into the recess formed in the outer surface of the thermoplastic fluoropolymer layer is performed after the step of thermally bonding the thermoplastic fluoropolymer layer to the outer surface of the fluoropolymer layer.

7. The method of claim 1 wherein thermally bonding the thermoplastic fluoropolymer layer to the outer surface of the fluoropolymer layer is performed prior to providing the recess in the outer surface of the thermoplastic fluoropolymer layer.

8. The method of claim 1 wherein thermally bonding the thermoplastic fluoropolymer layer to the outer surface of the fluoropolymer layer is performed concurrent with providing the recess in the outer surface of the thermoplastic fluoropolymer layer.

9. A method for manufacturing a joint in a medical electrical lead, the joint being between an inner surface of an insulative sidewall of the lead and an outer surface of a tubular fluoropolymer layer, the method comprising:
  thermally bonding a thermoplastic fluoropolymer layer to the outer surface of the fluoropolymer layer, and providing an outer surface of the thermoplastic fluoropolymer layer with a recess formed therein;
  assembling a layer of another material into the recess formed in the outer surface of the thermoplastic fluoropolymer layer;
  thereafter adhesively bonding the other material layer in the recess formed in the outer surface of the thermoplastic fluoropolymer layer to the inner surface of the insulative sidewall;
  wherein the other material layer and the insulative sidewall are each formed from a material that does not comprise a fluoropolymer; and
  wherein the recess formed within the thermoplastic fluoropolymer layer comprises a spiral groove.

10. The method of claim 9 wherein the step of adhesively bonding the other material layer to the inner surface of the insulative sidewall comprises placing an adhesive between the inner surface of the insulative sidewall and the layer of the other material into the recess formed in the outer surface of the thermoplastic fluoropolymer layer.

11. The method of claim 9 wherein the step of adhesively bonding the other material layer to the inner surface of the insulative sidewall comprises placing an adhesive between the inner surface of the insulative sidewall and the layer of the other material, wherein the adhesive is formed from a material that does not comprise a fluoropolymer.

12. The method of claim 9 wherein the step of assembling the layer of the other material into the recess formed in the outer surface of the thermoplastic fluoropolymer layer is performed after the step of thermally bonding the thermoplastic fluoropolymer layer to the outer surface of the fluoropolymer layer.

13. The method of claim 9 wherein thermally bonding the thermoplastic fluoropolymer layer to the outer surface of the fluoropolymer layer is performed prior to providing the recess in the outer surface of the thermoplastic fluoropolymer layer.

14. The method of claim 9 wherein thermally bonding the thermoplastic fluoropolymer layer to the outer surface of the fluoropolymer layer is performed concurrent with providing the recess in the outer surface of the thermoplastic fluoropolymer layer.

* * * * *